(12) United States Patent
Cude

(10) Patent No.: US 9,700,703 B2
(45) Date of Patent: Jul. 11, 2017

(54) GUIDEWIRE INSERTION TOOL

(71) Applicant: J. Michael Cude, College Grove, TN (US)

(72) Inventor: J. Michael Cude, College Grove, TN (US)

(73) Assignee: Coeur, Inc., Lebanon, TN (US)

( * ) Notice: Subject to any disclaimer, the term of this patent is extended or adjusted under 35 U.S.C. 154(b) by 426 days.

(21) Appl. No.: 13/777,443

(22) Filed: Feb. 26, 2013

(65) Prior Publication Data

US 2014/0237798 A1 Aug. 28, 2014

(51) Int. Cl.
*B23Q 3/18* (2006.01)
*A61F 2/30* (2006.01)
*A61M 25/01* (2006.01)
*A61M 25/09* (2006.01)
*A61M 25/06* (2006.01)

(52) U.S. Cl.
CPC .. *A61M 25/09041* (2013.01); *A61M 25/0662* (2013.01); *A61F 2/3094* (2013.01); *A61F 2/30907* (2013.01); *A61F 2002/30919* (2013.01); *A61M 25/0152* (2013.01); *A61M 25/0905* (2013.01); *A61M 2025/015* (2013.01); *A61M 2025/091* (2013.01); *A61M 2025/09058* (2013.01); *B23Q 3/18* (2013.01); *B23Q 3/186* (2013.01); *Y10T 29/49826* (2015.01); *Y10T 29/49895* (2015.01); *Y10T 29/49897* (2015.01); *Y10T 29/49902* (2015.01)

(58) Field of Classification Search
CPC ...... A61M 25/09041; A61M 2025/015; A61M 25/0152; A61M 2025/09058; A61M 25/0662; A61M 25/091; A61M 25/0905; B23Q 3/18; B23Q 3/186; Y10T 29/49826; Y10T 29/49895; Y10T 29/49897; Y10T 29/49902; A61F 2002/30919; A61F 2/30907; A61F 2/3094
USPC ........................ 29/464, 465, 468; 604/1, 528
See application file for complete search history.

(56) References Cited

U.S. PATENT DOCUMENTS

| | | | | | |
|---|---|---|---|---|---|
| 2,927,378 | A | * | 3/1960 | Godfrey et al. | 33/197 |
| 3,072,955 | A | * | 1/1963 | Mitchell | 294/171 |
| 3,537,451 | A | * | 11/1970 | Dale et al. | 604/165.03 |
| 4,079,738 | A | * | 3/1978 | Dunn et al. | 604/164.05 |
| 4,772,266 | A | * | 9/1988 | Groshong | 604/164.05 |
| 4,829,999 | A | * | 5/1989 | Auth | 606/1 |
| 5,137,517 | A | * | 8/1992 | Loney et al. | 604/159 |
| 5,141,497 | A | * | 8/1992 | Erskine | 604/164.05 |
| 5,161,534 | A | * | 11/1992 | Berthiaume | 600/434 |
| 5,234,002 | A | * | 8/1993 | Chan | 600/585 |
| 5,320,613 | A | * | 6/1994 | Houge et al. | 604/533 |
| 5,544,926 | A | * | 8/1996 | Ravencroft | 294/217 |
| 5,730,231 | A | * | 3/1998 | Racodon | B25D 3/00 16/431 |
| 5,860,190 | A | * | 1/1999 | Cano | A47G 21/02 16/422 |

(Continued)

*Primary Examiner* — Christopher Besler
*Assistant Examiner* — Bayan Salone
(74) *Attorney, Agent, or Firm* — Hahn Loeser & Parks LLP

(57) ABSTRACT

A guidewire insertion tool includes a sidewall defining a passageway having a first open end and a second open end and a neck therebetween. The passageway tapers from the first and second open ends to the neck. The sidewall has a slit extending longitudinally along the sidewall. A tab is adjacent one of the first or second open ends for removing the tool from a guidewire through the slit.

15 Claims, 12 Drawing Sheets

(56) References Cited

U.S. PATENT DOCUMENTS

| | | | | |
|---|---|---|---|---|
| 5,951,518 A * | 9/1999 | Licata et al. | ................ | 604/161 |
| 5,978,699 A * | 11/1999 | Fehse et al. | ................ | 600/434 |
| 5,989,210 A * | 11/1999 | Morris | ............ | A61B 17/32075 |
| | | | | 604/22 |
| 6,317,968 B1 * | 11/2001 | Kawamura | ................ | 29/755 |
| 6,517,518 B2 * | 2/2003 | Nash et al. | ................ | 604/164.02 |
| 7,717,865 B2 * | 5/2010 | Boutillette | ...... | A61M 25/09041 |
| | | | | 600/585 |
| 8,246,585 B2 * | 8/2012 | Schennib | ................ | 604/256 |
| 8,850,676 B2 * | 10/2014 | Schmitt | ................ | 29/44 |
| 8,986,226 B2 * | 3/2015 | Cude | ................ | 600/585 |
| 2002/0032432 A1 * | 3/2002 | Nash et al. | ................ | 604/533 |
| 2002/0198497 A1 * | 12/2002 | Nash et al. | ................ | 604/164.01 |
| 2003/0225397 A1 * | 12/2003 | Baechtold | ................ | 606/1 |
| 2004/0073193 A1 * | 4/2004 | Houser et al. | ................ | 604/528 |
| 2006/0094987 A1 * | 5/2006 | van Erp et al. | ................ | 600/585 |
| 2012/0210569 A1 * | 8/2012 | Schmitt | ................ | 29/700 |
| 2013/0190731 A1 * | 7/2013 | Cude | ................ | 604/528 |

* cited by examiner

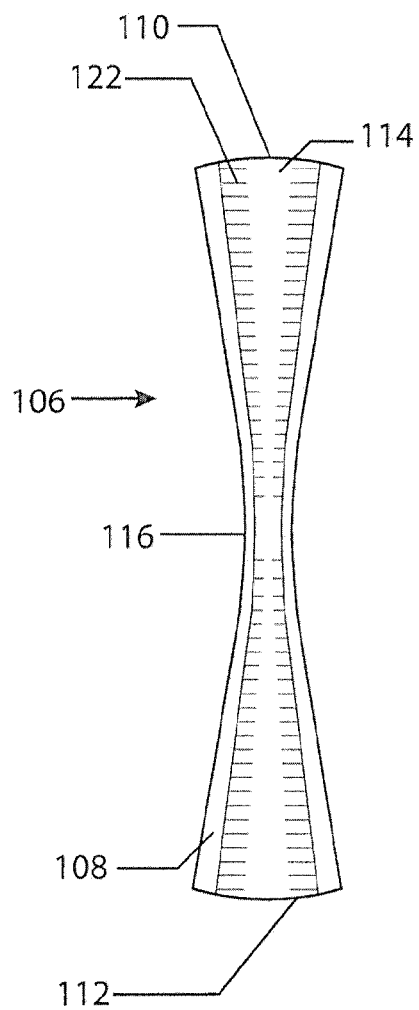
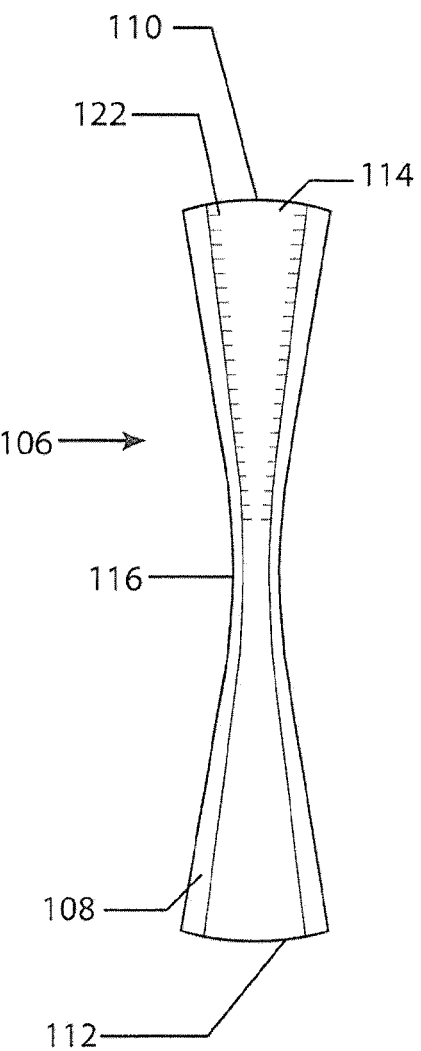
FIG. 6A                    FIG. 6B

GUIDEWIRE INSERTION TOOL

BACKGROUND

Medical guidewires are devices that may be used to assist in the positioning of catheters, stents, and other medical devices in circulatory, lymphatic, and other systems. Typically, a user will insert the guidewire percutaneously, and proceed to feed the guidewire through the vasculature system. The user may navigate the guidewire through branches in the vasculature. In one application, when the guidewire reaches a desired location, a catheter, stent, or other device may be advanced over the path defined by the guidewire and subsequently placed at the desired location.

The width of a guidewire is generally correlated with the width of the vasculature system of intended use. For example, diameters from 0.010" to 0.038" are common guidewire sizes in the medical field. The length of a guidewire may be limited by the type of procedure and/or the desired location within the vasculature. Lengths ranging from 50 cm to 450 cm are common. As a result, guidewires are often long and slender and it depends upon the skill of a particular user to manipulate and advance the guidewire in use.

SUMMARY

A guidewire insertion tool includes a sidewall defining a passageway having a first open end and a second open end and a neck therebetween. The passageway tapers from the first and second open ends to the neck. The sidewall has a slit extending longitudinally along the sidewall. A tab is adjacent one of the first or second open ends for removing the tool from a guidewire through the slit.

The tab may extend away from the first open end. The tab may include gripping structure to aid in removal of the tool from a guidewire.

A plurality of protrusions may extend from the sidewall into the passageway for engaging a catheter tube inserted therein. The plurality of protrusions may include a plurality of fingers. The plurality of protrusions may be adjacent one of said first open end and said second open end. The plurality of protrusions may be circumferentially positioned about the passageway. The plurality of protrusions may be disposed between one of the first open end and the second open end and the neck. The plurality of protrusions may extend toward the neck.

A stop may be disposed in the neck, the stop having a reduced diameter in the passageway for restricting the passage of articles smaller in diameter than the neck but larger in diameter than the stop. The stop may extend circumferentially about the neck. The stop may be positioned between one of the first open end and the second open end and the neck. The stop may be sloped towards the neck.

An indicator may be adjacent one of the first open end or the second open end for indicating that one of a catheter tube or a guidewire should be inserted therein.

A method for inserting a guidewire into a catheter tube is also disclosed.

BRIEF DESCRIPTION OF DRAWINGS

FIG. 6A is a cross-sectional view of a tool according to a further embodiment.

FIG. 6B is a view similar to FIG. 6A of a tool according to an alternative further embodiment.

DETAILED DESCRIPTION

Figure 1:
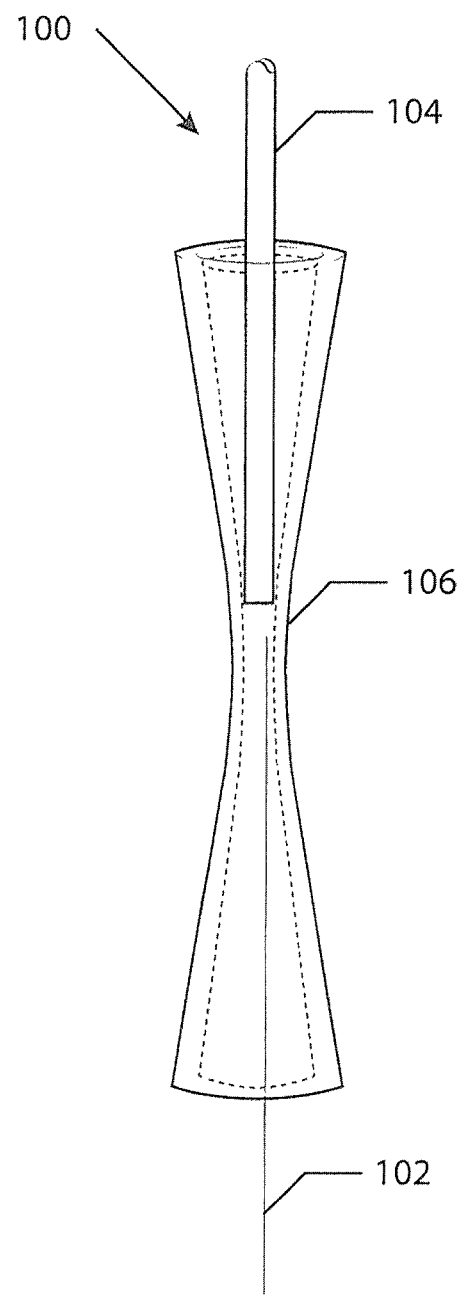
FIG. 1 is a perspective view of a guidewire insertion assembly.

There is Illustrated in FIG. 1 a guidewire insertion assembly 100 including a guidewire 102, a catheter tube 104, and an insertion tool 106. The guidewire 102 is provided, for example, for guiding through the catheter tube 104 and into a body lumen (not shown) and is sized to fit within the catheter tube 104. The catheter tube 104 is sized to receive the guidewire. The catheter tube 104 uses may include drainage, measurement, administration of fluids, access for surgical instruments, or any other suitable medical procedure. The diameter of the catheter tube 104 may vary according to utility and, for example, may be in a range from 1-10 Fr.

Figure 2:
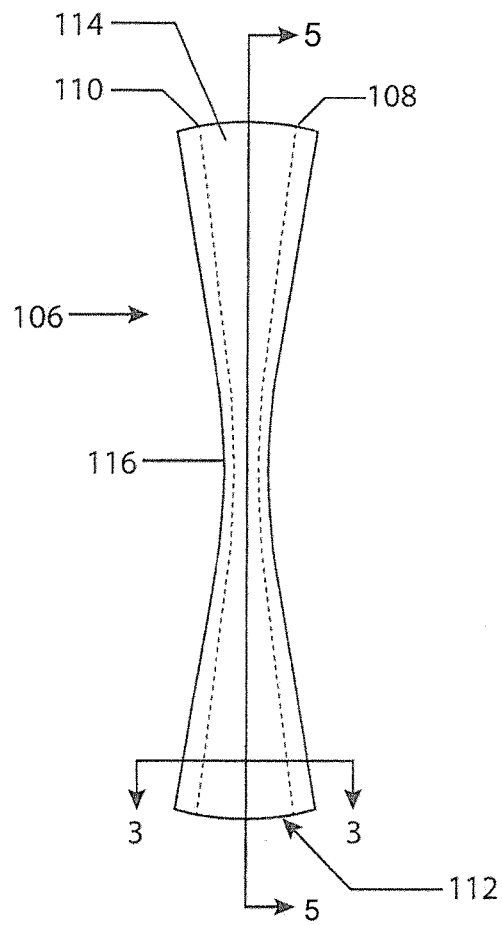
FIG. 2 is a side view of the tool of FIG. 1.

As shown in FIG. 2, the insertion tool 106 for directing the guidewire 102 into the catheter tube 104 has a sidewall 108, a first open end 110, a second open end 112, a through passageway 114. The through passageway 114 tapers to a narrow neck 116 between the first open end 110 and the second open end 112. In the illustrated example, each of the first open end 110 and the second open end 112 are generally funnel shaped and may each result in an opening generally larger in diameter than the associated catheter tube 104 or the guidewire 102, respectively, to be used during a medical procedure. In the illustrated embodiment, the insertion tool 106 is thus generally hourglass-shaped, although such is not required. In one use, this arrangement facilitates the guidewire 102 to be guided into the catheter tube 104, allowing for insertion of the guidewire 102 into the catheter tube 104. In the illustrated example, the first open end 110 and the second open end 112 are generally of similar size, although such is not required. It is contemplated that the diameter, the taper angle, the length, or any other suitable geometrical feature of the first open end 110 or the second open end 112 may vary relative to one another to accommodate the respective guidewire 102 or catheter tube 104 as desired.

While the insertion tool 106 is generally described as receiving the catheter tube 104 in the first open end 110 and the guidewire 102 in the second open end 112, it must be understood that this is only one example. In at least one example, the insertion tool 106 may receive the catheter tube 104 in the second open end 112 and the guidewire 102 in the first open end 110. Further, it is contemplated that in at least one example, the insertion tool 106 may receive either of the catheter tube 104 and the guidewire 102 in either of the first open end 110 and the second open end 112. The insertion tool 106 may be either unidirectional or bidirectional. In a unidirectional arrangement, the first open end 110 may be marked and adapted to receive the catheter tube 104, and the second open end 112 may be marked and adapted to receive the guidewire 102. For example, adjacent the first open end 110 or between the first open end 110 and the neck 116 may be structure for supporting, indicating, or receiving the catheter tube 104. Adjacent the second open end 112 or between the second open end 112 and the neck 116 may be structure for supporting, indicating, or receiving the guidewire 102. For further example, in a bidirectional arrangement, the insertion tool 106 may be substantially symmetrical about the neck 116, and the guidewire 102 and the catheter tube 104 may be inserted in either the first open end 110 or the second open end 112.

In at least one embodiment, the insertion tool 106 is made of silicone; however, other materials are contemplated, including rubber, polymer resin, flexible plastic, and other flexible materials suitable for medical devices. In these embodiments, the flexible material may aid in the use of the insertion tool 106 in a surgical operation and provides for the insertion tool 106 to be removed easily from the guidewire 102. Further, according to other various embodiments, the insertion tool 106 may be made of rigid or semi-rigid materials such as rigid plastic or other materials as desired.

Figure 3:
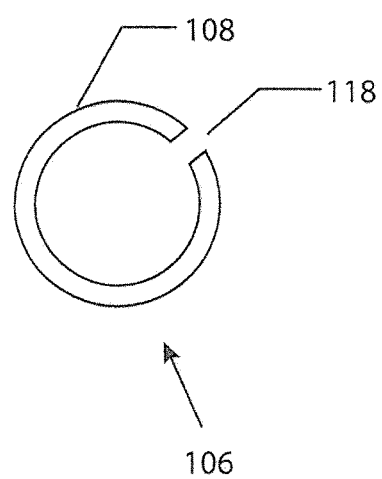
FIG. 3 is a cross-sectional view of the tool of FIG. 2 taken along line 3-3.

In the illustrated embodiment shown in FIGS. 1-3, the sidewall 108 has a substantially constant thickness, although such is not required. It is contemplated that the sidewall 108 may vary in thickness. For one example, the insertion tool 106 may be generally cylindrically shaped on the exterior, having a varying thickness of the sidewall 108 to define the first open end 110, the second open end 112, and the reduced neck 116 therebetween. Other arrangements are also contemplated.

As shown in FIG. 3, the insertion tool 106 has a substantially circular cross-section and includes a slit 118 or cutaway that extends along the length of the insertion tool 106. The slit 118 is sized so that the guidewire 102 may slide therethrough so the insertion tool 106 may be removed from the guidewire 102.

Figure 4A:
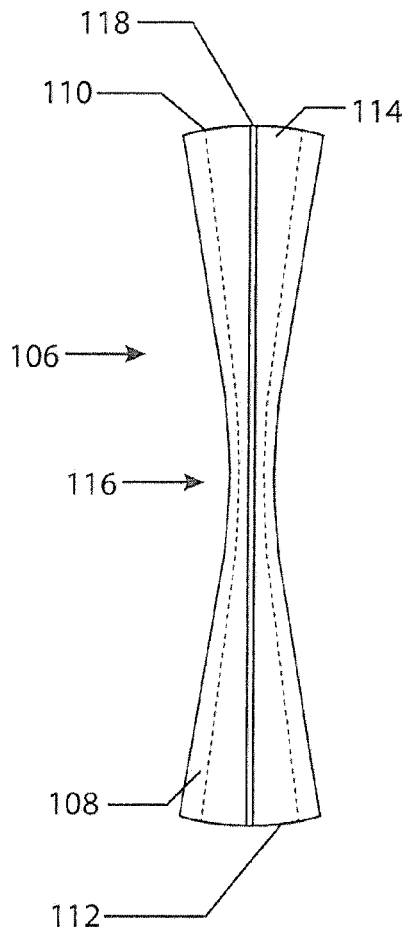
FIG. 4A is a rotated side view similar to FIG. 2.
Figure 4B:
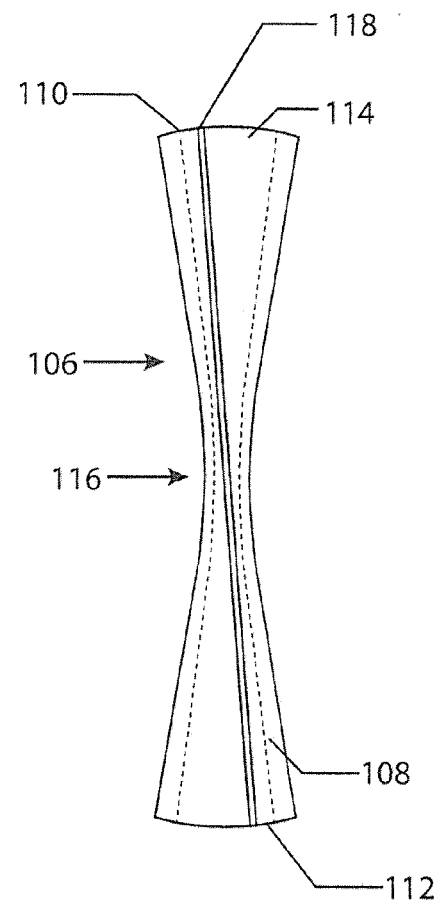
FIG. 4B is a view similar to FIG. 4A of a tool according to an alternative embodiment.

FIGS. 4A-B illustrate various forms that the slit 118 may take. According to the first variation illustrated in FIG. 4A, the slit 118 extends parallel to an axis of the insertion tool 106 between the first open end 110 and second open end 112. In an alternative arrangement, illustrated in FIG. 4B, the slit 118 is not parallel to the axis of the insertion tool 106 but extends circumferentially as well as axially along the sidewall 108 of the insertion tool 106, resulting in a spiraling arrangement. Other arrangements, such as zigzag, or otherwise irregular slits are also contemplated.

Figure 5A:
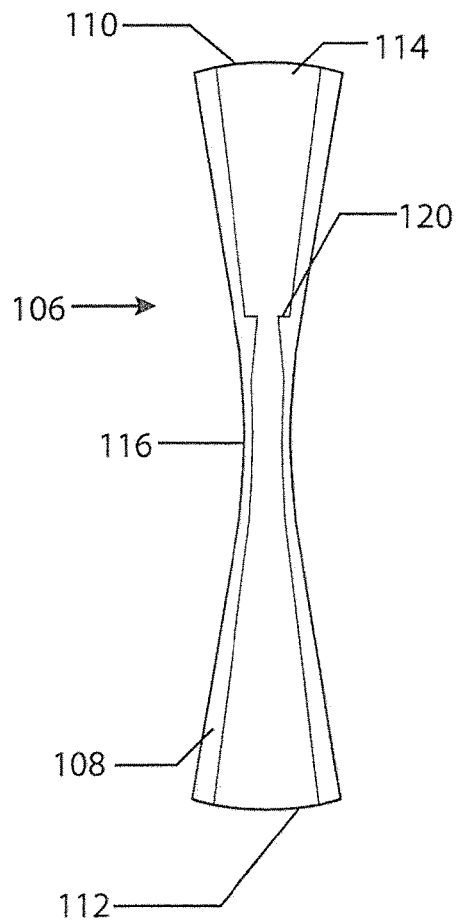
FIG. 5A is a cross-sectional view of the tool of FIG. 2 taken along line 5-5.
Figure 5B:
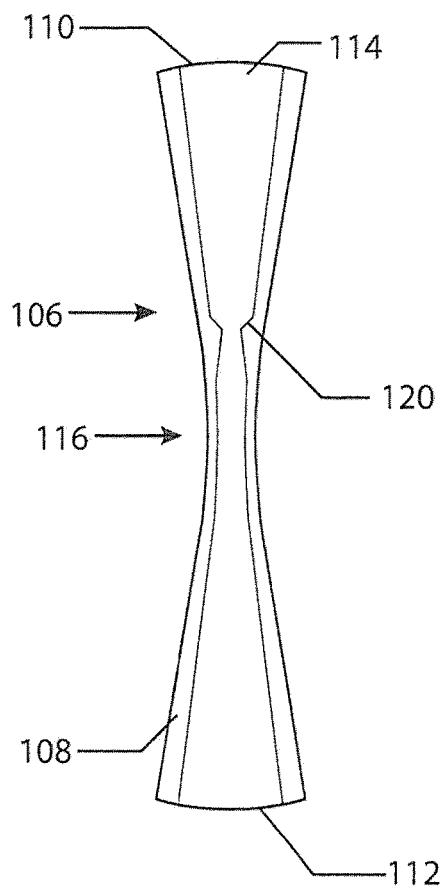
FIG. 5B is a view similar to FIG. 5A of a tool according to an alternative embodiment.
Figure 5C:
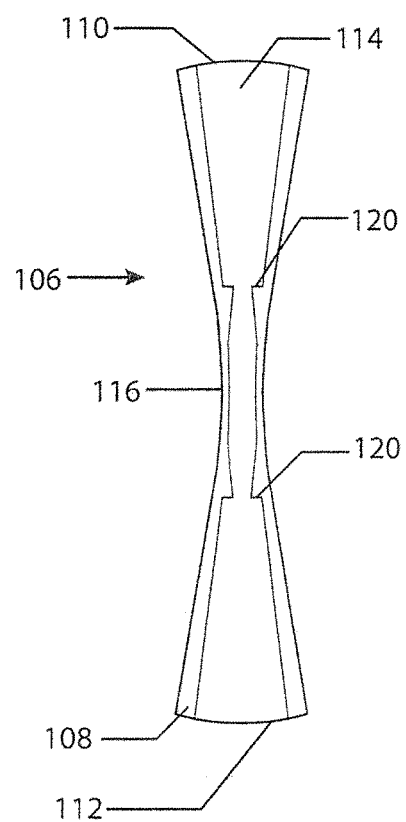
FIG. 5C is a view similar to FIG. 5A of a tool according to another alternative embodiment.

FIGS. 5A-C illustrate alternative embodiments of the insertion tool 106. In these embodiments, there is positioned adjacent and circumferentially about the neck 116 of the insertion tool 106 a stop 120 that reduces the diameter of the through passageway 114 at the neck. For example, in one use, this allows the guidewire 102 to pass therethrough but not the catheter tube 104. The size of the passageway 114 at the stop 120 may correspond to a specific guidewire 102 and catheter tube 104 sized so that the guidewire 102 properly passes into the catheter tube 104 as desired. The stop 120 may provide tactile feedback to a user to indicate when a device, such as the catheter tube 104, has been fully inserted into the insertion tool 106. This may, for example, indicate to the user to next insert the guidewire 102 into the insertion tool 106.

In these illustrated arrangements, the stop 120 extends substantially about the entire circumference of the neck 116, although such is not required. It is also contemplated that the stop 120 may extend only about a portion of the neck 116 or may include a plurality of stops 120 about the neck 116, so as to restrict the passage of articles smaller in diameter than neck 116 but larger in diameter than the stop 120.

According to the embodiment illustrated in FIG. 5A, the stop 120 is positioned adjacent the neck 116 nearest the first open end 110 that receives the catheter tube 104. The other side of the neck 116, towards the second open end 112, that receives the guidewire 102 does not include any stop. In this arrangement, the guidewire 102 can be inserted without encountering the stop 120, while a catheter tube 104 inserted into the through passageway 114 through the first open end 110 will engage the stop 120, thereby providing the tactile feedback to the user and/or bracing the catheter tube 104 against the tool 106.

Further according to this arrangement shown in FIG. 5A, the stop 120 has a flat top surface substantially perpendicular to the axis of the insertion tool 106 so that when catheter tube 104 of various sizes engage the stop 120 they are prevented from further entering the neck 116.

According to another embodiment, as shown in FIG. 5B, the stop 120 may be sloped inward towards the neck 116. This arrangement may be advantageous as it allows a catheter tube 104 inserted into the passageway 114 to be guided into the center of the tool 106 and the through passageway 114. This arrangement may allow various sizes of catheter tubes 104 to be utilized with a single apparatus as differently sized catheter tubes 104 will stop at different points along the stop 120 as the diameter of the passageway 114 equals the outer diameter of the catheter tube 104. It is contemplated that in one use this will center the catheter tube 104, allowing the guidewire 102 to be easily inserted into the catheter tube 104.

It must be understood that various other arrangements of the stop 120 are contemplated. The stop may include an upward slope, a step, a curved edge, or any other shapes or combination of shapes, as desired to engage an article inserted into the tool 106.

For further example, according to the arrangement illustrated in FIG. 5C, the stop 120 may be positioned on both sides of the neck 116. Providing the stop 120 on both sides of the neck 116 allows the insertion tool 106 to be used in varying arrangements as the catheter tube 104 will engage the stop 120 from both the first 112 and second 114 ends. However, in this arrangement, as the guidewire 102 may engage one of the stops 120, it may, therefore, be preferably to provide the stops 120 at an angle, such as the arrangement shown in FIG. 5B, although such is not required, so that the guidewire 102 is guided through the neck 116 and into the catheter tube 104.

Figure 6C:
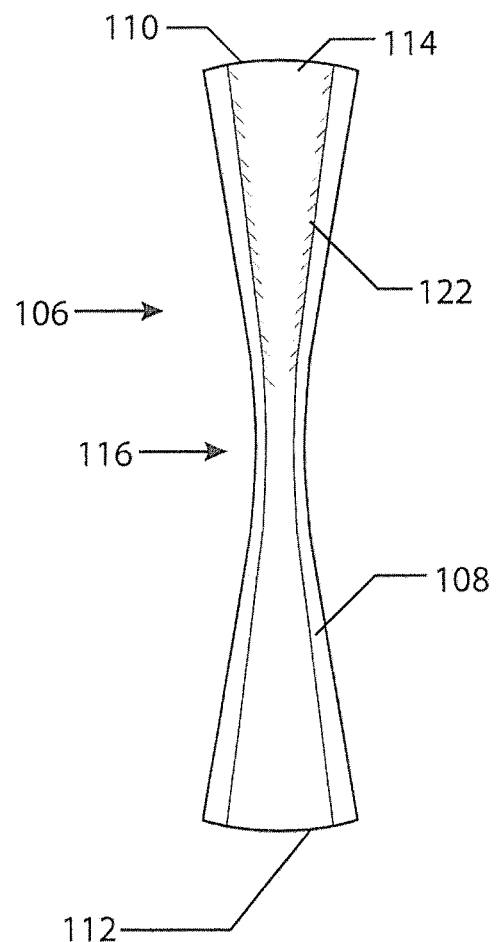
FIG. 6C is a view similar to FIG. 5A of a tool according to another alternative further embodiment.

There is illustrated in FIGS. 6A-C various arrangements of other embodiments. According to these arrangements, a number of protrusions 122, such as fingers or hairs as will be described below, protrude from the sidewall 108 about the circumference of the insertion tool 106 into the through passageway 114 and are positioned to engage the catheter tube 104, or other article, as it enters the insertion tool 106 and provide resistance against the catheter tube 104 or other article from drawing out of the insertion tool 106, thereby freeing the user's hand from holding the insertion tool 106.

These protrusions 122 may take various forms, as illustrated in FIGS. 6A-C and FIGS. 11 and 12.

In the arrangement illustrated in FIG. 6A, the insertion tool 106 may selected for a specific diameter or diameter range for the catheter tube 104, corresponding to the protrusions 122 that extend into the through passageway 114 to receive the catheter tube 104. The protrusions 122 according to this arrangement may vary in length so that as to form a uniform central column defined by the ends of the protrusions 122, although such is not required. In use as the catheter tube 104 is inserted into the passageway 114 the protrusions 122 engage the catheter tube 104 and restrain it from moving relative to the insertion tool 106 without further applied force so that the user may not have to hold the catheter tube 104 and insertion tool 106 together. Further according to this arrangement, insertion tool 106 is bidirectional and the protrusions 122 are provided on both sides of the insertion tool 106 and the central column is sized to allow the guidewire 102 to pass to the neck 116 without being obstructed by the protrusions 122.

According to the arrangement illustrated in FIG. 6B, the protrusions 122 may have a fixed length and define a central column having a decreasing or variable diameter. According to this embodiment, the catheter tube 104 may be inserted into the insertion tool 106 and will be funneled to the neck 116 by the protrusions 122. Further, catheter tubes 104 having varying diameters will engage the protrusions 122 at different depths, helping to guide smaller catheter tubes 104 to the neck 116 and allowing the guidewire 102 to be directed into the neck 116. As with the protrusions 122 in FIG. 6A, the catheter tube 104 may be held in place by the protrusions 122, freeing the user's hands from holding the insertion tool 106.

The arrangements illustrated in FIGS. 6A-B provide that the protrusions 122 have either a variable length and a fixed central column or a fixed length and a variable central column. However, it is contemplated that the protrusions 122 and central column defined thereby may vary in size and shape as desired.

According to the arrangement illustrated in FIG. 6C, the protrusions 122 may be angled towards the neck 116. By angling the protrusions 122 towards the neck 116, the protrusions 122 will provide stronger resistance to the catheter tube 104 pulling out of the insertion tool 106 while allowing the catheter tube 104 to more easily be inserted. If provided on both sides of the neck 116, the angled protrusions 122 may also help guide the guidewire 102 to the neck 116. According to other arrangements, the protrusions 122 may also be angled away from the neck 116 or various protrusions 122 may be provided at different angles.

As illustrated between FIGS. 6A and 6B and 6C, the protrusions 122 may be present on one or both sides of the neck 116. Providing protrusions 122 on both sides of the neck 116 allows the catheter tube 104 and guidewire 102 to be inserted at either the first 110 and second 112 ends indiscriminately. In an arrangement where hairs are provided on one side of the neck 116, it is expected that the protrusions 122 would be provided on the side receiving the catheter tube 104, although other arrangements are contemplated.

Figure 7A:
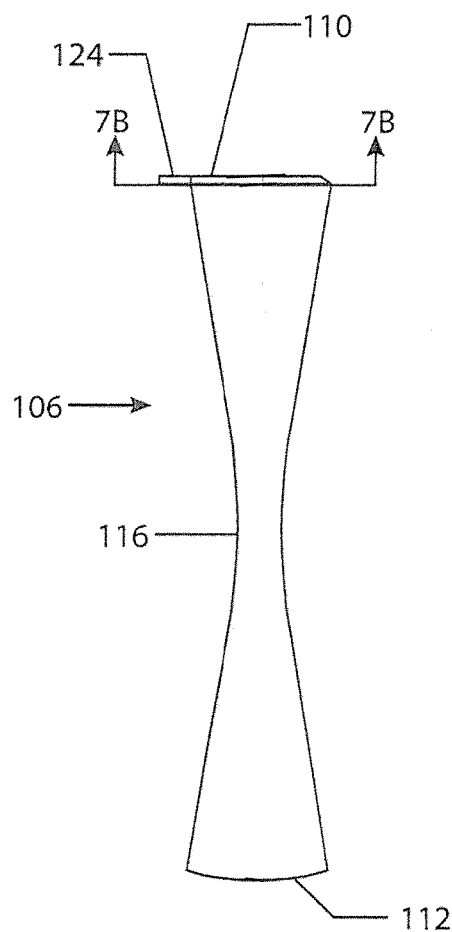
FIG. 7A is a side view of a tool according to an additional embodiment.

There is shown in FIG. 7A another embodiment in which the insertion tool 106 includes a tab 124 positioned adjacent the first open end 110. The tab 124 may be useful for removing the insertion tool 106 from an article inserted therein, such as the catheter tube 104 and/or guidewire 102. Once the catheter tube 104 and guidewire 102 have been inserted into the insertion tool 106, the practitioner may grasp the tab 124 and draw the insertion tool 106 away from the guidewire 102, passing the guidewire 102 through the slit 118. The tab 124 is shown adjacent the first open end 110 for illustrative purposes, but it will be understood that the tab 124 may be provided on either end or any location suitable to facilitate removal of the tool 106 from an article inserted therein.

Figure 7B:
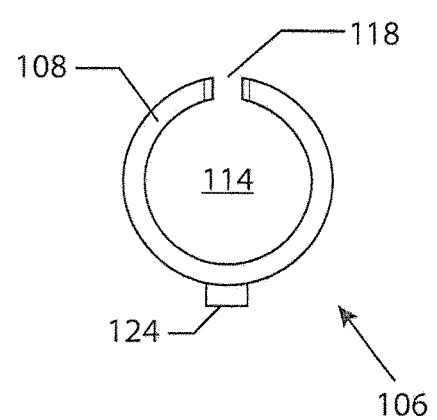
FIG. 7B is a cross-sectional view of the tool of FIG. 7B taken along line 7B-7B.

As shown in FIG. 7B, the tab 124 may be provided opposite the slit 118. However, it may be desirable to place the tab 124 adjacent the slit 118 or at another position along the circumference of the insertion tool 106. Further according to this illustration, the tab 124 is integrally formed with the sidewall 108, although such is not required. The tab 124 preferably protrudes from the insertion tool 106 at a size and shape easily grasped by the user and may include ridges, divets, or other structure to aid the user in grasping the tab 124 to remove the insertion tool 106.

It is contemplated that the tab 124 may be provided between the first open end 110 and the neck 116, between the second open end 112 and the neck 116, at the neck 116, adjacent one of the ends, or any other suitable location. Further, the tab 124 is shown as parallel to the first open end 110, but it is contemplated that the tab may run along the side of the insertion tool 106 and be at any suitable angle or orientation. Finally, multiple tabs 124 are contemplated, either on opposing ends 110 and 112 or at various positions about the circumference of the insertion tool 106.

Figure 8:
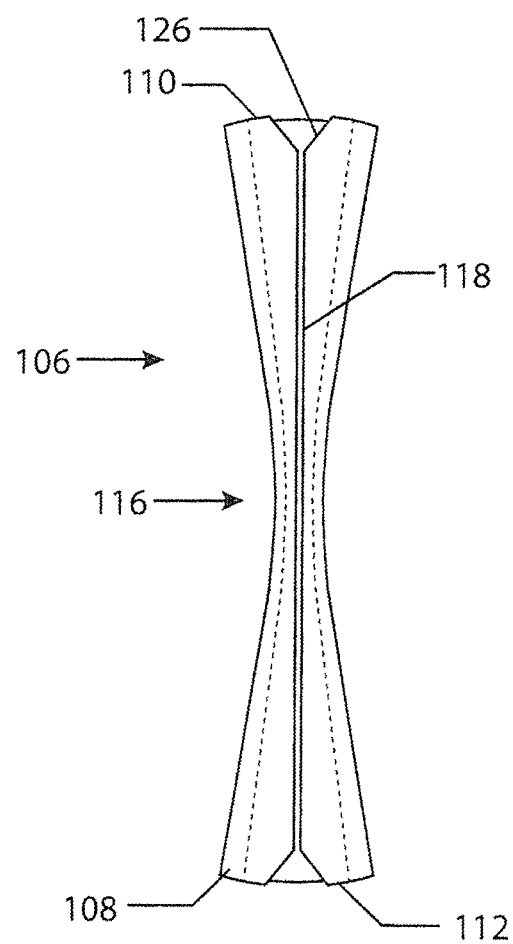
FIG. 8 is a rotated side view of the tool of FIG. 7A.

As shown in FIG. 8, a notch 126 may be provided along the slit 118 at either or both of the first open end 110 and/or the second open end 112. This notch 126 may be provided to aid in the removal of the insertion tool 106 from the guidewire 102 and/or catheter tube 104. For example, when the insertion tool 106 is removed from the guidewire 102, the guidewire 102 may be guided along the notch 126 to the slit 118 to facilitate removal.

Figure 9:
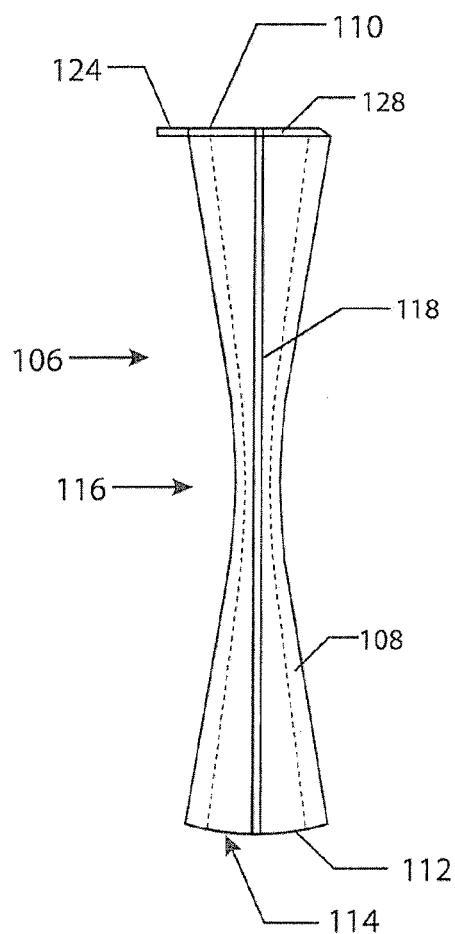
FIG. 9 is a side view of a tool according to another additional embodiment.

There is illustrated in FIG. 9 another embodiment in which the insertion tool 106 includes an indicator 128 on the first open end 110 indicating that the catheter tube 104 should be inserted therein. In the illustrated arrangement, the indicator 128 is a rigid component extending away from the first open end 110 for receiving the catheter tube 104. The indicator 128 may also include a tab 124 as illustrated in FIG. 9. In order to facilitate the removal of the insertion tool 106 from the catheter, the indicator 128 illustrated may also include a slot (not shown). In another arrangement, the indicator 128 provided on one end may indicate that the guidewire 102 should be inserted into that end.

Figure 10:
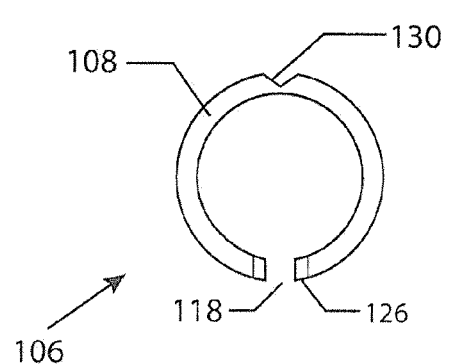
FIG. 10 is a first end view of the tool of FIG. 9.

As shown in FIG. 10, the insertion tool 106 may include a groove 130 opposite the slit 118 that allows for easy opening of the insertion tool 106. According to this arrangement, the groove 130 is v-shaped and extends into the sidewall 108.

Figure 11:
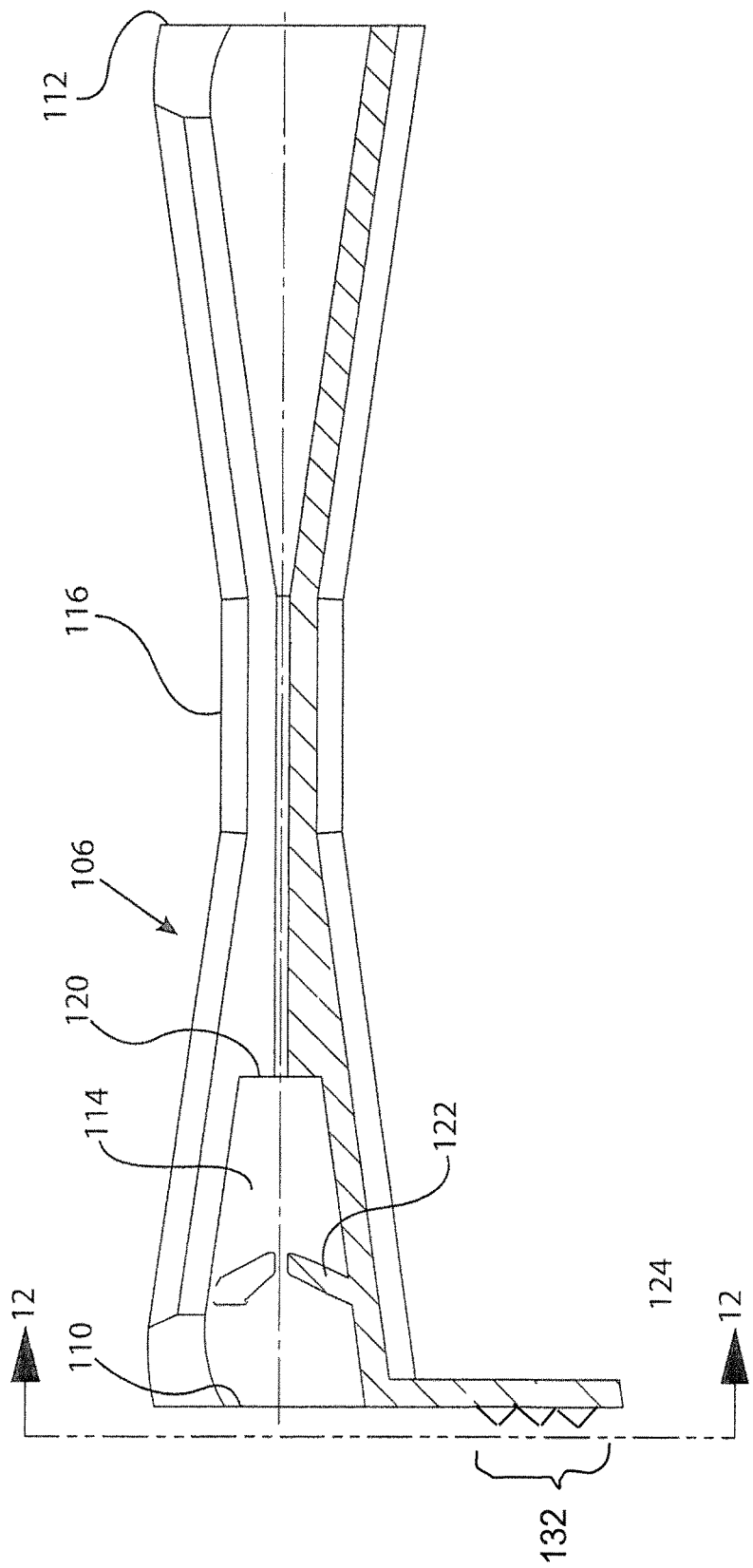
FIG. 11 is a cross-sectional view of the tool of FIG. 9.
Figure 12:
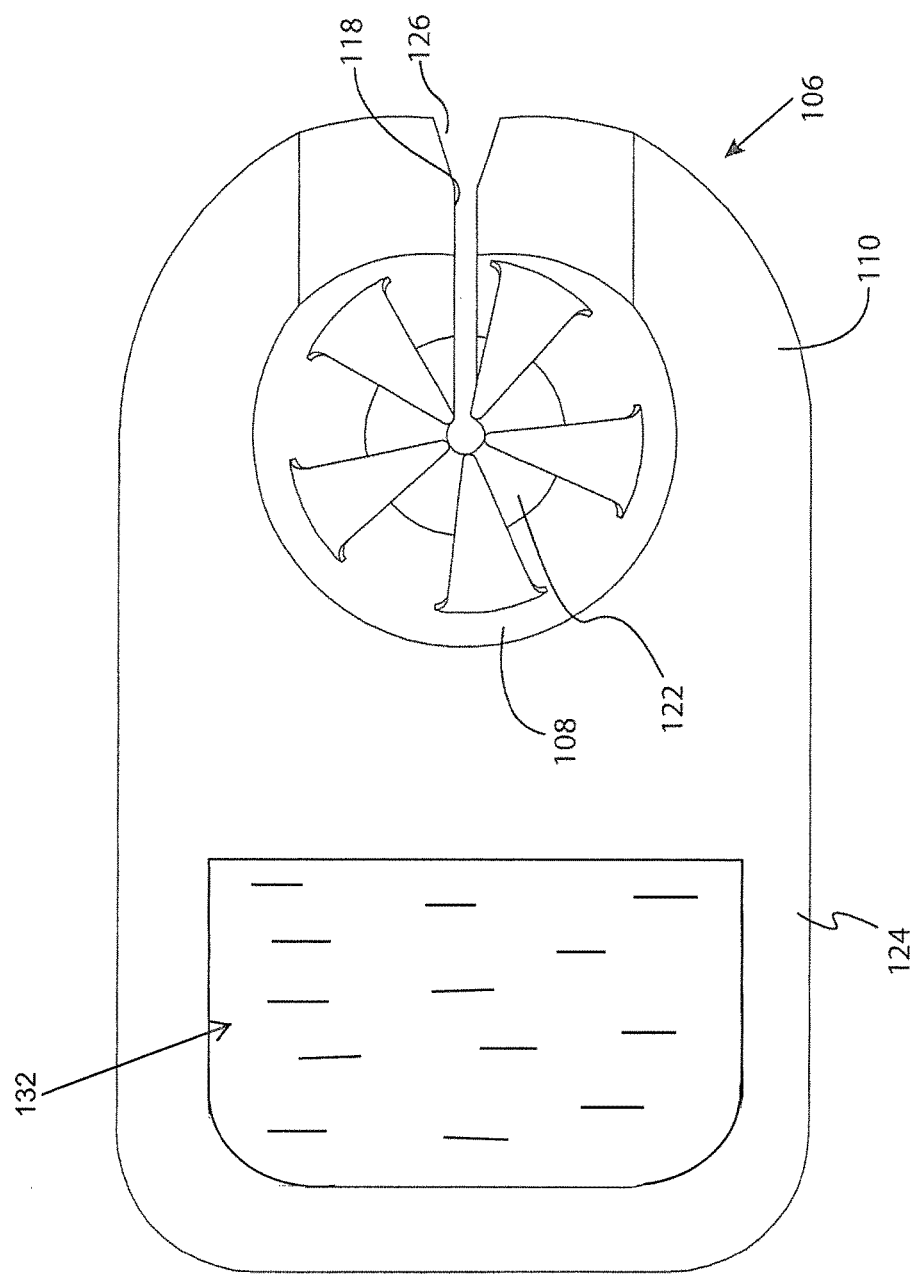
FIG. 12 is an enlarged second end view of the tool of FIG. 11 taken along line 12-12.

As best shown in FIGS. 11 and 12, the illustrated arrangement the plurality of protrusions 122 or fingers extending from the sidewall 108 into the passageway 114 about or near the first open end 110 so as to engage the catheter tube 104 as it is inserted into the insertion tool 106. Also provided at the first open end 110 is the tab 124 for aiding in the removal of the insertion tool 106 from the guidewire 102 and catheter tube 104.

In this arrangement, five protrusions 122 are provided in circular symmetry about the passageway 114 and taper in width as they extend into the passageway 114, although such is not required. The protrusions 122 are angled towards the neck 116 of the insertion tool 106 to provide resistance against drawing the catheter tube 104 from the insertion tool 106. The protrusions 122 are sized, spaced, and angled so that the catheter tube 104 may be easily inserted into the insertion tool 106 while resisting removal.

As best shown in FIG. 12, the tab 124 for removing the insertion tool 106 from the guidewire 102 and catheter tube 104 is substantially rectangular with a width equal to the outer diameter of the insertion tool 106 and a length greater than the outer diameter of the insertion tool 106. A long axis of the tab 124 extends away from the first open end 110 opposite the slit 118. It must be understood that it is contemplated that the tab 124 may be positioned at various angles relative to the slit 118, up to and including 90° relative to the position of the slit 118 on the insertion tool 106. The tab 124 may include a textured surface 132 or other gripping structure for securely grasping the tab 124 or to otherwise aid in removal of the insertion tool 106 from the guidewire 102.

A method for inserting the guidewire 102 into the catheter tube 104 with the tool 106 follows. The method includes the steps of providing the insertion tool 106 having opposite first open end 110 and second open end 112 and the passageway 114 passing therethrough. The insertion tool 106 tapers from the first open end 110 to the narrow neck 116 and from the second open end 112 to the neck 116. The slit 118 is provided along the sidewall 108 of the insertion tool 106.

Next, the catheter tube 104 is selected having an inner diameter for receiving the guidewire 102. The catheter tube 104 is inserted into the first open end 110 of the insertion tool 106 and advanced to the neck 116. The guidewire 102 is inserted into the second open end 112 of the insertion tool 106. Finally, the guidewire 102 is advanced, passing through the neck 116 and into the catheter tube 104.

The insertion tool 106 may then be removed from the catheter tube 104 and guidewire 102. The practitioner grips the insertion tool 106 and draws it opposite the direction of the slit 118, with the catheter tube 104 withdrawing from the first open end 110 and the guidewire 102 passing through the slit 118, thereby allowing the insertion tool 106 to be completely removed.

According to one variation on this method, the insertion tool 106 is provided with the tab 124 positioned adjacent one of the first 110 or second 112 ends and opposite the slit. In order to remove the insertion tool 106 from the catheter tube 104 and guidewire 102, the practitioner grips the tab 124 and draws the insertion tool 106 in a direction opposite the slit 118.

In yet at least one other embodiment, the insertion tool 106 may be provided with the plurality of protrusions 122 within the through passageway 114 that may engage the catheter tube 104, or other device to be inserted therein, as it is inserted into the insertion tool 106.

While principles and modes of operation have been explained and illustrated with regard to particular embodiments, it must be understood, however, that this may be practiced otherwise than as specifically explained and illustrated without departing from its spirit or scope.

What is claimed is:

1. A guidewire insertion tool comprising:
    a sidewall defining a passageway having a first open end and a second open end and a neck therebetween, said passageway tapering from said first and second open ends to said neck, said sidewall having a slit extending longitudinally along said sidewall;
    a tab adjacent one of said first or second open ends for removing the tool from a guidewire through said slit;
    and a stop disposed in said neck, said stop sloping towards the neck and extending circumferentially about the entire circumference of the neck and having a reduced diameter in said passageway that is smaller than a diameter of said neck for restricting passage of articles smaller in diameter than said neck but larger in diameter than said stop, wherein the reduced diameter of the stop allows the guidewire to pass therethrough.

2. The tool of claim 1 where said tab extends away from said first open end.

3. The tool of claim 1 where said tab includes gripping structure to aid in removal of said tool from a guidewire.

4. The tool of claim 1 further comprising:
    a plurality of protrusions extending from said sidewall into said passageway for engaging a catheter tube inserted therein.

5. The tool of claim 4 where the plurality of protrusions includes a plurality of fingers.

6. The tool of claim 4 where the plurality of protrusions are adjacent one of said first open end and said second open end.

7. The tool of claim 4 where said plurality of protrusions are circumferentially positioned about said passageway.

8. The tool of claim 4 where said plurality of protrusions is disposed between one of said first open end and said second open end and said neck.

9. The tool of claim 4 where said plurality of protrusions extend toward said neck.

10. The tool of claim 1 where said stop is positioned between one of said first open end and said second open end and said neck.

11. The tool of claim 1 further comprising:
    an indicator adjacent one of said first open end or said second open end for indicating that one of a catheter tube or a guidewire should be inserted therein.

12. A device for inserting a guidewire into a catheter tube comprising:
    a tool including a sidewall defining a passageway having a means for receiving a catheter tube and a means for receiving a guidewire and a neck therebetween, said passageway tapering to said neck, said sidewall having a means for passage of the guidewire from said tool during removal of said tool, and a means for restricting passage of articles smaller in diameter than said neck but larger in diameter than said means for restricting, where said means for restricting is disposed in said neck, slopes towards said neck, extends circumferentially about the entire circumference of the neck, and has a diameter in said passageway that is smaller than a diameter of said neck, wherein the diameter of the means for restricting allows the guidewire to pass therethrough.

13. The device of claim 12 further comprising: a means for removing said tool from said guidewire.

14. A guidewire insertion tool comprising:
    a sidewall defining a passageway having a first open end and a second open end and a neck therebetween, said passageway tapering from said first and second open ends to said neck, said sidewall having a slit extending longitudinally along said sidewall;
    a tab adjacent one of said first or second open ends for removing the tool from a guidewire through said slit; and
    a plurality of protrusions extending from said sidewall into said passageway for engaging a catheter tube inserted therein, where said plurality of protrusions are circumferentially positioned about said passageway, extend radially into said passageway, and are angled axially towards said neck, wherein the protrusions provide resistance to the catheter tube pulling out of the insertion tool while allowing the catheter tube to be inserted.

15. The tool of claim 14 further comprising: a stop disposed in said neck, the stop having a reduced diameter in said passageway for restricting passage of articles smaller in diameter than said neck but larger in diameter than said stop.

* * * * *